United States Patent
Hu et al.

(10) Patent No.: US 9,085,588 B2
(45) Date of Patent: Jul. 21, 2015

(54) METHODS OF PREPARING ICOTINIB AND ICOTINIB HYDROCHLORIDE, AND INTERMEDIATES THEREOF

(71) Applicant: BETTA PHARMACEUTICALS CO., LTD., Zhejiang (CN)

(72) Inventors: Shaojing Hu, Beijing (CN); Wei Long, Beijing (CN); Fei Wang, Beijing (CN); Zongquan Li, Beijing (CN)

(73) Assignee: Betta Pharmaceuticals Co., Ltd., Hangzhou (CN)

( * ) Notice: Subject to any disclaimer, the term of this patent is extended or adjusted under 35 U.S.C. 154(b) by 0 days.

(21) Appl. No.: 14/355,142

(22) PCT Filed: Dec. 28, 2012

(86) PCT No.: PCT/CN2012/087802
§ 371 (c)(1),
(2) Date: Apr. 29, 2014

(87) PCT Pub. No.: WO2013/064128
PCT Pub. Date: May 10, 2013

(65) Prior Publication Data
US 2014/0343283 A1 Nov. 20, 2014

(51) Int. Cl.
*C07D 323/00* (2006.01)
*C07D 491/056* (2006.01)
*C07D 405/04* (2006.01)
*C07D 325/00* (2006.01)

(52) U.S. Cl.
CPC .......... *C07D 491/056* (2013.01); *C07D 323/00* (2013.01); *C07D 325/00* (2013.01); *C07D 405/04* (2013.01)

(58) Field of Classification Search
CPC ............................ C07D 323/00; C07D 325/00
See application file for complete search history.

(56) References Cited

U.S. PATENT DOCUMENTS 7,078,409 B2 * 7/2006 Zhang et al. .................. 514/267

FOREIGN PATENT DOCUMENTS

WO   WO 2007138613   12/2007
WO   WO 2010/003313   1/2010

* cited by examiner

*Primary Examiner* — Erich A Leeser
(74) *Attorney, Agent, or Firm* — Weisun Rao; Greenberg Traurig, LLP

(57) ABSTRACT

The present invention relates to the technical field of medicine, and specifically provides methods for preparing Icotinib, Icotinib hydrochloride, and intermediates thereof. These methods avoid the use of phosphorus oxychloride, thereby greatly reducing the emission of pollutants, which is of major benefits to the economy and environment.

32 Claims, No Drawings

METHODS OF PREPARING ICOTINIB AND ICOTINIB HYDROCHLORIDE, AND INTERMEDIATES THEREOF

CROSS-REFERENCE TO RELATED APPLICATION

This application is a national phase application and claims benefit under 35 U.S.C. § 371 of PCT/CN2012/087802, filed on Dec. 28, 2012, which in turn claims priority to international application No. PCT/CN2011/081586, filed on Oct. 31, 2011, the contents of which are incorporated herein by reference in their entireties.

FIELD OF THE INVENTION

The present invention relates to the technical field of medicine, and in particular to preparation methods of Icotinib intermediates, Icotinib and Icotinib hydrochloride.

BACKGROUND OF THE INVENTION

Tyrosine kinase receptors are trans-membrane proteins involved in signal conversion. They propagate growth factor signals, which cascade to control cell proliferation, mutation, angiogenesis, apoptosis and other important features, from the surface of cellular to inner cellular. One class of such tyrosine kinase receptors, epidermal growth factor receptor (EGFR) tyrosine kinases, are over-expressed in many human tumor or cancers, including tumor or cancers of brain, lung, liver, bladder, chest, head and neck, esophagus, gastrointestinal track, breast, ovary, cervix, or thyroid.

EGFR is expressed in many types of tumor cells. After binding with its ligands including epidermal growth factor (EGF) or Transforming Growth Factor-α (TGF-α), EGFR activates tyrosine kinases in cytoplasmic domains and results in transphosphorylation of the tyrosine at EGFR hydroxyl terminal Then, EGFR controls multiple gene transcription through different signal transduction channels, thereby regulating cell proliferation, differentiation, and apoptosis. EGFR is closely related to tumor metastasis, vascular proliferation, and chemotherapy drug resistance.

Various molecular and cellular biology and clinical studies have demonstrated or proved that EGFR kinase inhibitor can block EGFR signal transductions related to cancer cell proliferation, metastasis and others responses, and thus achieve clinical anti-tumor therapeutic effects.

Two oral EGFR kinase inhibitors with similar chemical structures are Gefitinib (Iressa, AstraZeneca), approved by the U.S. FDA for advanced non-small cell lung cancer treatment in 2003, and Erlotinib Hydrochloride (Tarceva, Roche and OSI), approved by the U.S. FDA for advanced non-small cell lung cancer and pancreatic cancer treatment in 2004.

EGFR tyrosine kinase inhibitor (TKI) is a popular research field of a new generation of targeted anti-tumor drug in the world. U.S. Pat. No. 7,078,409B2 and CN130568C disclose preparation methods of Icotinib, and WO2010/003313 discloses a preparation method of Icotinib hydrochloride. However, the methods disclosed by U.S. Pat. No. 7,078,409B2 and CN130568C require use of highly toxic reagent, i.e, Chlorinating agent, such as $(COCl)_2$ or phosphorus oxychloride. These highly toxic Chlorinating agents, especially Chlorinating agent containing phosphorus, are very difficult or costly to be completely removed in the later reactions. Therefore, the existing synthetic methods not only are very costly but also cause severe environment pollution problems, and present a significant threat to the health of producers and users. The preparation method disclosed in WO2010/003313 uses metal catalysts, which are also costly and difficult to be separated or recovered. Furthermore, any direct emission of such metal and phosphine ligand will cause severe environment pollutions.

The intermediary compounds designed by the present invention are used for preparing Icotinb or Icotinib hydrochloride. These preparation methods avoid use of high-toxic reagents, proceed in mild reaction conditions, and thus are easier, more economic, lower-toxic and safer than synthetic methods currently known in the art.

DESCRIPTION OF THE INVENTION

The present invention overcomes the problems of the existing technology and provides methods for preparing intermediates of Icotinib, i.e., compound A, compound B, and compound C, as well as methods for preparing Icotinib and Icotinib hydrochloride using those intermediates. These novel methods are more environmental friendly and economic, and can proceed in relatively mild reaction conditions and reduce environment pollutions.

For the convenience of illustration in the present application, compound 1 refers to 1,8-bis-(para-toluenesulfonate)-3,6-dioxo-octane is named; compound 2 refers to 3,4-benzo-12-crown-4-benzonitrile; compound A refers to 6-nitro-3,4-benzo-12-crown-4-benzonitrile; compound B refers to 6-amino-3,4-benzo-12-crown-4-benzonitrile; compound C refers to

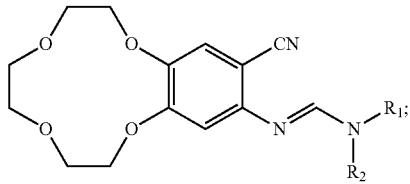

compound C1 refers to

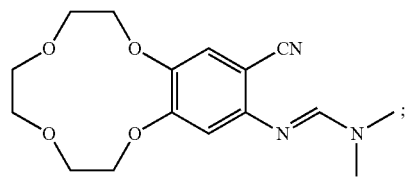 [SMILES: CN(C)/C=N/c1cc2c(cc1C#N)OCCOCCOCCO2]

Icotinib refers to 4-[(3-ethynylphenyl)amino]-quinazoline and [6,7-b]-12-crown-4; Icotinib hydrochloride refers to 4-[(3-ethynylphenyl)amino]-quinazoline and [6,7-b]-12-crown-4 hydrochloride. For these compounds, compound A can be used to prepare compound B, compound B can be used to prepare compound C, compound C can be used to prepare Icotinib or Icotinib hydrochloride, and all of the compounds A, B, and C can be used to prepare Icotinib and Icotinib hydrochloride. Chemical structures of Compounds 1, 2, A, B, C, and C1, Icotinib and Icotinib hydrochloride are shown below, respectively:

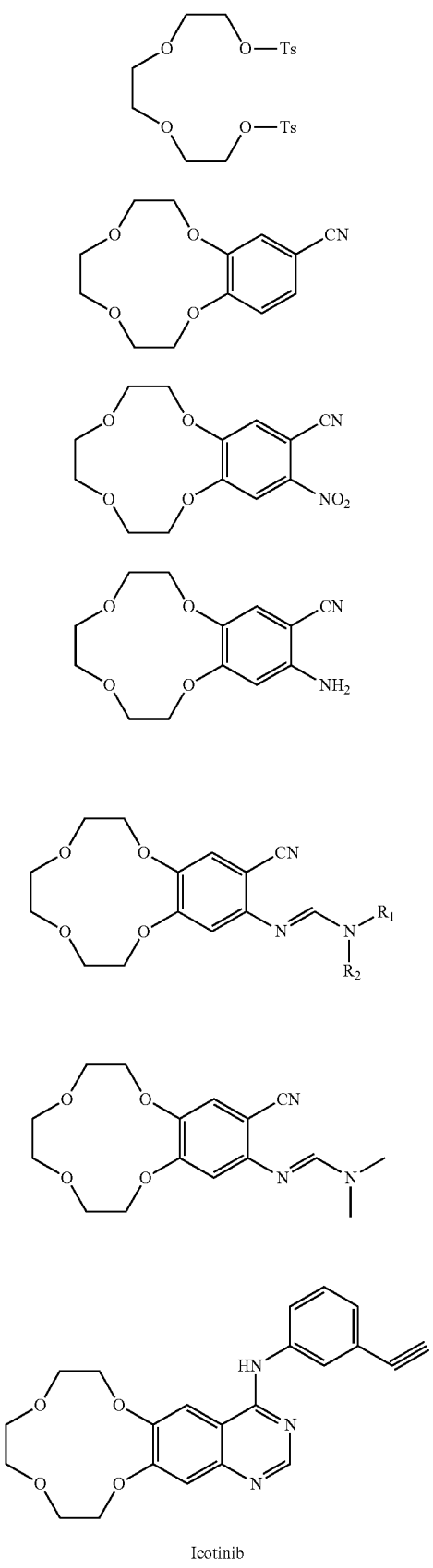

Icotinib

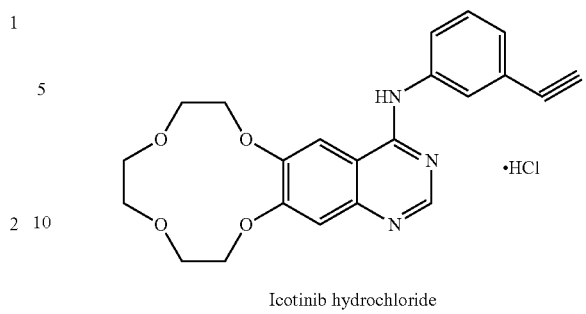

Icotinib hydrochloride

The present invention firstly provides a compound of formula A, B or C:

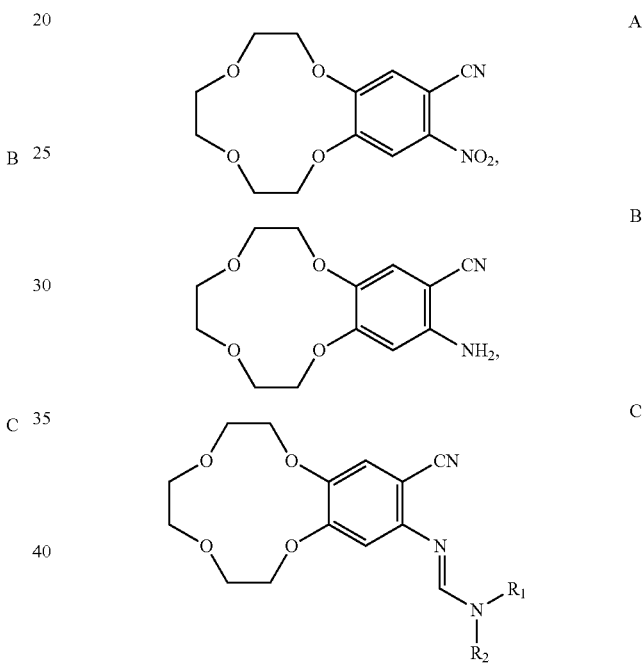

wherein, each $R_1$ and $R_2$ independently is methyl, ethyl, propyl, or isopropyl; or, $R_1$ and $R_2$, together with the N atom to which they are attached, form a 3 to 7-membered ring. Preferably, each of $R_1$ and $R_2$ independently is methyl or ethyl.

The present invention further provides some preferred technical solutions with regard to compound C:

Preferably, $R_1$ and $R_2$ are methyl.

Preferably, $R_1$ and $R_2$ are ethyl.

Preferably, $R_1$ and $R_2$, together with the N atom to which they are attached, form a 3, 4 or 5-membered ring.

Preferably, $R_1$ and $R_2$, together with the N atom to which they are attached, form a 5, 6 or 7-membered ring.

The present invention further provides a method for preparing a compound of formula C, wherein compound C is prepared from compound B, and the method comprises the following step:

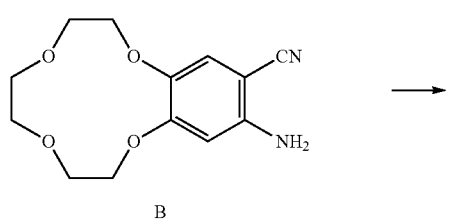

B

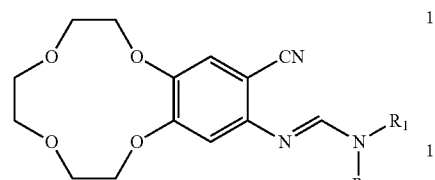

C

The present invention further provides some preferred technical solutions for the preparation method of a compound of formula C.

Preferably, the methods comprise the following step:

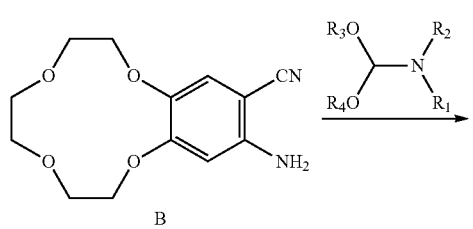

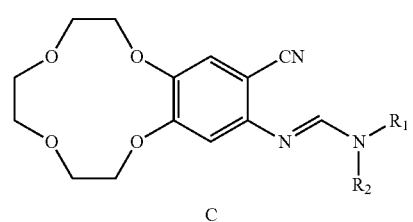

C wherein, each of $R_3$ and $R_4$ independently is methyl, ethyl, propyl, isopropyl, n-butyl, sec-butyl, tert-butyl, isobutyl, or benzyl; or $R_3$ and $R_4$ form a 3 to 7-membered ring.

Preferably, each of $R_3$ and $R_4$ independently is methyl, ethyl, isopropyl, tert-butyl, or benzyl.

Preferably, $R_3$ and $R_4$ are methyl.

Preferably, $R_3$ and $R_4$ are ethyl.

Preferably, compound B and

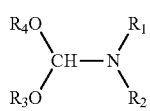

react in dioxane or toluene under reflux state.

Preferably, the molar ratio of compound B and

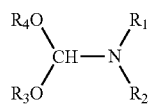

is 1:1.5 to 1:2.8.

Preferably, the molar ratio of compound B and

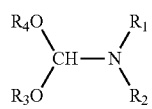

is 1:2.0 to 1:2.5.

Preferably, 11-30 mmol of compound B and 25-67 mmol of

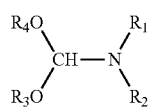

react in 140-180 mL of dioxane for 10-15 hours under reflux state.

Preferably,

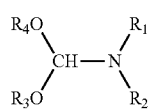

is N,N-dimethylformamide dimethyl acetal, N,N-dimethylformamide diethyl acetal, or N,N-dimethylformamide di-tert-butyl acetal.

The present invention further provides a method for preparing a compound of formula B, wherein the compound of formula B is prepared from a compound of formula A, and the method comprises the following step:

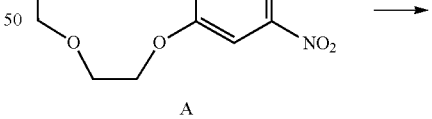

A

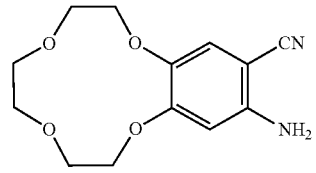 [SMILES: N#Cc1cc2c(cc1N)OCCOCCOCCO2]

B

The present invention further provides some preferred technical solutions for the preparation method of a compound of formula B:

Preferably, compound A reacts with proton-donating agent, metal hydrides, hydrazine, or alkali metal amide solution via catalytic hydrogenation reaction or metal-involved reduction reaction; the metal is Mg, Al, Zn, Fe, Sn, Pb, or Cu; the proton-donating agent is Acetic acid, formic acid, and/or trifluoroacetic acid; the catalyst applied in catalytic hydrogenation reaction is palladium/carbon or raney nickel; the metal hydride is sodium hydride or potassium hydride; and the alkali metal is sodium or potassium.

Preferably, compound A, ferrous powder, and solution of acetic acid in methanol are fully mixed and heated to reflux until the reaction is complete.

Preferably, 85 mmol-0.2 mol of compound A, 0.45-0.71 mol of ferrous powder, and 900-1200 mL of acetic acid in methanol solution are fully mixed and then heated to reflux until the reaction is complete. As for the solution of acetic acid in methanol, the weight percent of acetic acid is 3-7%.

The present invention also provides a method for preparing Icotinib, where compound C and m-aminophenyl acetylene react in an organic acid.

The present invention further provides some preferred technical solutions for the preparation method of Icotinib:

Preferably, the molar ratio of compound C and m-aminophenyl acetylene is 1:1 to 1:2.

Preferably, the molar ratio of compound C and m-aminophenyl acetylene is 1:1 to 1:1.5.

Preferably, the organic acid is acetic acid, formic acid, and/or trifluoroacetic acid.

Preferably, compound C, m-aminophenyl acetylene, and the organic acid are fully mixed and then react at 70-150° C.

Preferably, the reaction temperature is 90-120° C. and the organic acid is acetic acid.

Preferably, N,N-dimethyl-N'-(6-cyano-3,4-benzo-12-crown-4)formamidine, m-aminophenyl acetylene and the acetic acid are fully mixed and then react at 70-150° C.

Preferably, 9-25 mmol of N,N-dimethyl-N'-(6-cyano-3,4-benzo-12-crown-4)formamidine, 15-21 mmol of m-aminophenyl acetylene, and 150-320 mL of acetic acid are fully mixed and then react at 90-120° C.

Preferably, 12-20 mmol of N,N-dimethyl-N'-(6-cyano-3,4-benzo-12-crown-4)formamidine, 17-20 mmol of m-aminophenyl acetylene, and 200-260 mL of acetic acid are fully mixed and then react at 95-105° C.

The present invention provides a novel method for preparing Icotinib hydrochloride. Icotinib can be prepared from compound C according to the methods described in the present invention. Then, the resulting Icotinib is dissolved in a lower alcohol, and hydrogen chloride (gas or liquid) is added while stirring. After the reaction is complete, the reaction mixture is filtrated.

The present invention further provides some preferred technical solutions for the preparation method of Icotinib hydrochloride:

Preferably, the lower alcohol is methanol, ethanol, and/or isopropanol.

Preferably, the amount of Icotinib is 1.3-2.6 mmol; the lower alcohol is methanol, the volume of which is 30-60 mL.

Preferably, the amount of Icotinib is 1.8 mmol; the lower alcohol is methanol, the volume of which is 40 mL.

As used herein, the term "proton-donating agent" refers to solvents that can offer proton, such as formic acid, acetic acid, trifluoroacetic acid, etc.

As used herein, the term "lower alcohol" refers to $C_1$-$C_4$ straight-chain or branched-chain unit or polyol, such as methanol, ethanol, propanol, isopropanol, butanol, or ethylene glycol, etc.

As used herein, the term "$R_1$ and $R_2$, together with the N atom to which they are attached" means that $R_1$ and $R_2$ can join together (with the oxygen atom attached to them) to form a 3 to 7-membered ring.

As used herein, the term "$R_3$ and $R_4$ form a 3 to 7-membered ring" means that $R_3$ and $R_4$ can join together (together with the oxygen atom attached to $R_3$, the carbon atom, and the oxygen atom attached to $R_4$) to form a 3 to 7-membered ring.

As used herein, the term "compound" refers to a compound or a pharmaceutically acceptable salt or solvate thereof.

The novel methods provided by the present invention can be a substitute for the methods disclosed in U.S. Pat. No. 7,078,409B2, CN130568C and WO2010/003313. Currently, the production of TKI type medicine is large. Our novel methods do not use high-toxic materials, and greatly reduce the emission of pollutants and environment pollution, thereby leading to significant economic benefits.

EXAMPLES

The present invention is further exemplified, but not limited to, by the following examples, which only aims to illustrate the preparation methods.

In the examples of the present invention, which only illustrate the embodiments to help people skilled in the art fully understand the invention but not restrict it. The techniques or methods of the embodiments in the present invention, unless expressly stated otherwise, are conventional techniques and methods in the art.

General Synthetic Scheme

Compound A provided by the present invention can be prepared, but not limited to, by the following synthetic scheme:

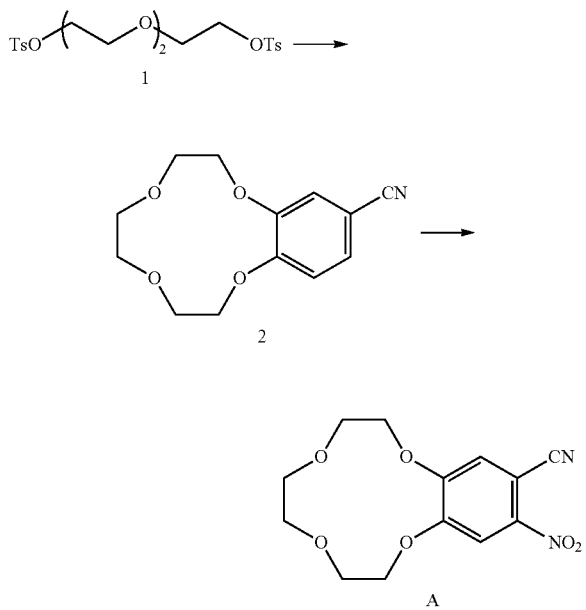

Compound B provided by the present invention can be prepared, but not limited to, by the following synthetic scheme:

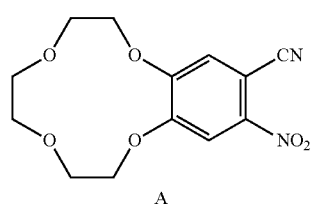

A

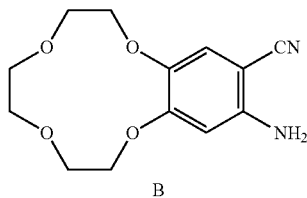

B

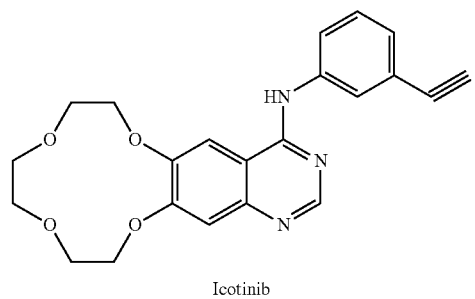

Icotinib wherein, each of $R_1$ and $R_2$ independently is selected from methyl, ethyl, propyl, and isopropyl; or $R_1$ and $R_2$, together with the N atom to which they are attached, form a 3 to 7-membered ring.

Icotinib hydrochloride can be prepared by a reaction between Icotinib and hydrochloric acid or hydrogen chloride gas:

Compound C provided by the present invention can be prepared, but not limited to, by the following synthetic scheme:

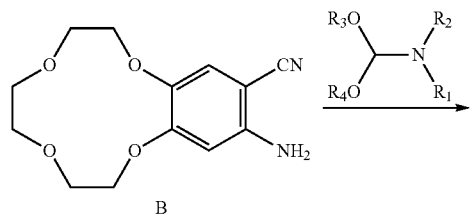

B

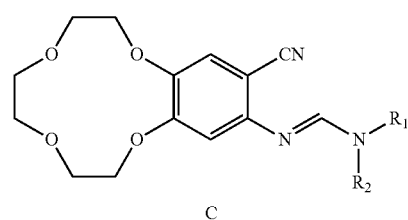

C

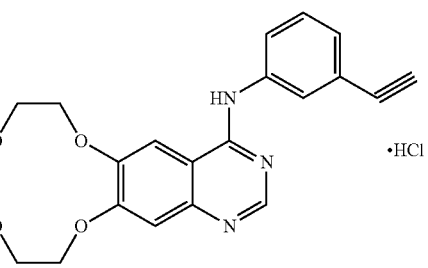

Icotinib $\xrightarrow{\text{hydrochloric acid or hydrogen chloride gas}}$

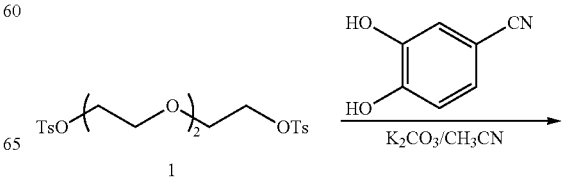

Icotinib hydrochloride wherein, each of $R_1$ and $R_2$ independently is methyl, ethyl, propyl, or isopropyl; or $R_1$ and $R_2$, together with the N atom to which they are attached, form a 3 to 7-membered ring.

each of $R_3$ and $R_4$ independently is selected from methyl, ethyl, propyl, isopropyl, n-butyl, sec-butyl, tert-butyl, isobutyl, and benzyl; or $R_3$ and $R_4$ together form a 3 to 7-membered ring.

Compound C provided by the present invention can be used for the direct synthesis of Icotinib:

Example 1

Synthesis of Compound A

1. Synthesis of Compound 2

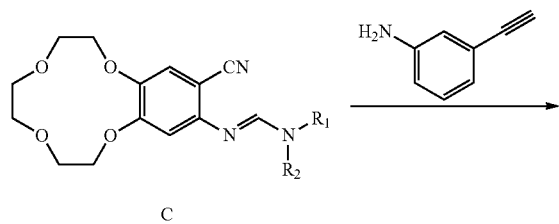

C $\xrightarrow{\text{H}_2\text{N}\text{—}\text{C}_6\text{H}_4\text{—}\text{C}\equiv\text{CH}}$ TsO(CH$_2$CH$_2$O)$_2$CH$_2$CH$_2$OTs

1

$\xrightarrow{\text{K}_2\text{CO}_3/\text{CH}_3\text{CN}}$ (with 3,4-dihydroxybenzonitrile)

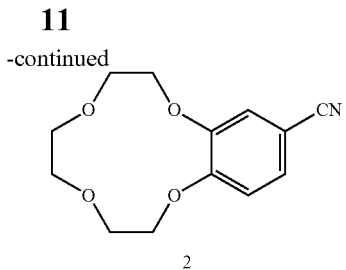

3,4-dihydroxyphenyl nitrile (79.5 g), potassium carbonate (272 g), and acetonitrile (6 L) were added into the 10 L of three-necked reaction flask. The reaction mixture was stirred to dissolve and heated to reflux. Then acetonitrile solution of compound 1 (compound 1, 200 g; acetonitrile, 2 L) was dropwise added under reflux condition. After its completion by HPLC monitoring, the reaction mixture was cooled to room temperature, filtered to remove the solvent. The resulting solid was dissolved in ethyl acetate and filtered. The filtrate was concentrated, and the remainder was dissolved in petroleum ether and evaporated. The residue was purified to give compound 2 (18.9 g).

$^1$HNMR (CDCl$_3$-δ ppm): 7.30~7.33 (m, 1H); 7.25 (s, 1H); 6.97-6.99 (d, 1H); 4.19~4.23 (m, 4H); 3.83~3.91 (m, 4H); 3.77 (s, 4H).

MS: (M+H)$^+$250

2. Synthesis of Compound A

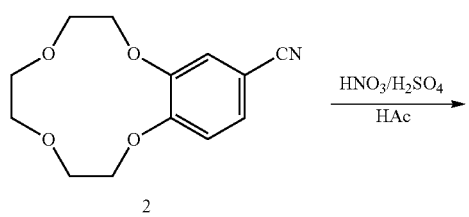

Compound 2 (41.6 g) was dissolved in acetic acid (580 mL) and heated to 30° C., fuming nitric acid (83 mL) was dropwise added to the solution. Then the concentrated sulfuric acid (42 mL) was dropwise added. The reaction mixture was cooled to room temperature and reacted overnight. After the reaction was complete by TLC monitoring, the reaction solution was spread into ice water till precipitate appeared, filtrated, and the solid was washed with cold water (500 mL×2), and dried in vacuum at 35° C. to give crude products of compound A (46 g), which was then purified by recrystallization with isopropanol to give compound A (33 g).

$^1$HNMR (CDCl$_3$-δ ppm): 7.90 (s, 1H); 7.36 (s, 1H); 4.33~4.369 (m, 4H); 3.87~3.89 (m, 4H); 3.737 (s, 4H).

Example 2

Synthesis of Compound B

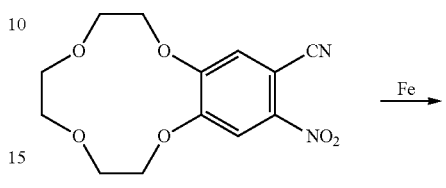

Compound A (32 g), ferrous powder (30.5 g), 5% acetic acid in methanol solution (1070 mL) were added into 2 L of reaction flask and heated to reflux. The reaction mixture was cooled and concentrated after the reaction was complete by TLC monitoring. The concentrated reaction solution was dissolved in ethyl acetate, filtrated and dried by anhydrous sodium sulfate (Na$_2$SO$_4$), the solvent was removed to give compound B (23 g).

$^1$HNMR (d$_6$-DMSO-δ ppm): 7.07 (s, 1H); 6.36 (s, 1H); 5.73 (s, 2H); 3.95~4.22 (m, 4H); 3.77~3.78 (m, 2H); 3.34~3.62 (m, 6H).

Example 3

Synthesis of Compound C1

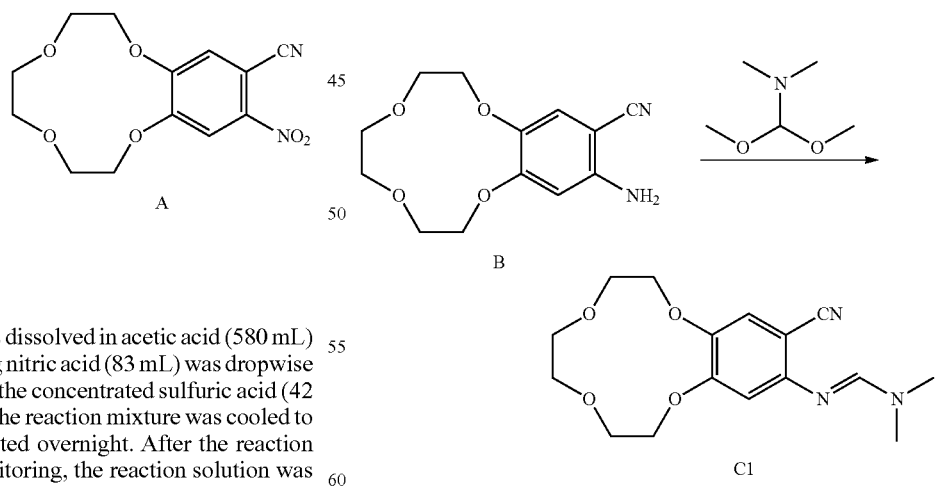

Compound B (5 g), N,N-dimethylformamide dimethyl acetal (5 g), and dioxane (160 mL) were added into 500 mL of three-necked flask, heated to reflux, and the reaction was monitored by TLC. The mixture was reacted for 12 hours. After its completion, the reaction solution was cooled to room temperature and evaporated to give compound C1 (5.8 g).

$^1$HNMR (CDCl$_3$-δ ppm): 7.56 (s, 1H); 7.15 (s, 1H); 6.51 (s, 1H); 4.12~4.18 (m, 4H); 3.89~3.91 (m, 2H); 3.78~3.80 (m, 6H); 3.07 (s, 6H)

Example 4

Synthesis of Icotinib

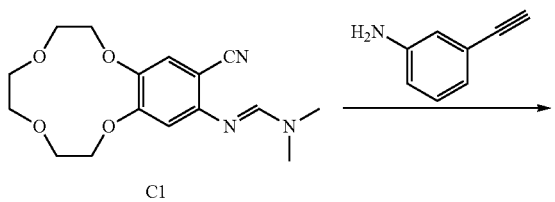

C1

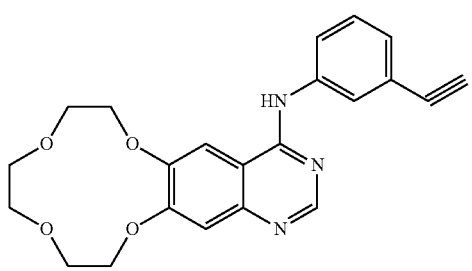

Icotinib

Compound C1 (5 g), m-aminophenyl acetylene (2.2 g), and acetic acid (230 mL) were added into 500 mL of reaction flask, heated to 100° C., and the reaction was monitored by TLC. After its completion, the reaction mixture was evaporated, methanol was added, and then the mixture was shock dispersed, filtrated, and washed with methanol to give Icotinib (5 g).

$^1$HNMR (d$_6$-DMSO-δ ppm): 11.98 (s, 1H); 9.50 (s, 1H); 8.53 (s, 1H); 8.14 (s, 1H); 8.04~8.05 (m, 1H); 7.90~7.92 (m, 1H); 7.38~7.42 (m, 1H); 7.31 (s, 1H); 7.20~7.22 (m, 1H); 4.29~4.30 (m, 4H); 4.21 (s, 1H); 3.74~3.81 (m, 4H); 3.64 (s, 4H); 1.91 (s, 3H);

Example 5

Synthesis of Icotinib Hydrochloride

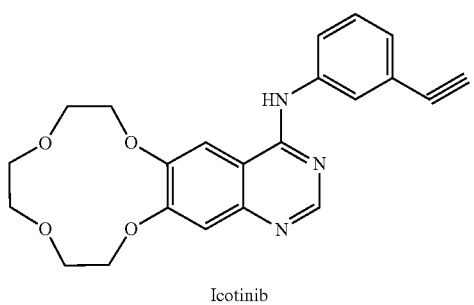

Icotinib

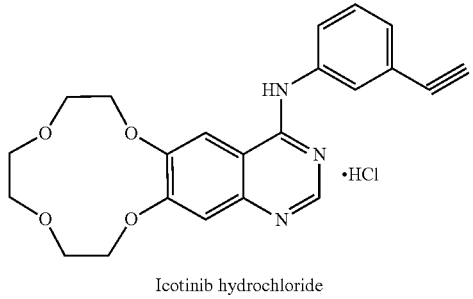

Icotinib hydrochloride

Icotinib (700 mg) and methanol (40 mL) were added into 100 mL of reaction flask, hydrogen chloride gas or concentrated hydrochloric acid was added while stirring. After its completion, the reaction mixture was filtrated to give crude products of Icotinib hydrochloride, which was then purified by recrystallization with isopropanol to give Icotinib hydrochloride (760 mg).

$^1$HNMR (d$_6$-DMSO-δ ppm): 11.37 (s, 1H); 8.87 (s, 1H); 8.63 (s, 1H); 7.90 (s, 1H); 7.78~7.80 (d, 1H); 7.48~7.52 (m, 1H); 7.40~7.41 (m, 2H); 4.36~4.38 (d, 4H); 4.30 (s, 1H); 3.75~3.81 (d, 4H); 3.61 (s, 4H);

Example 6

Synthesis of Compound B

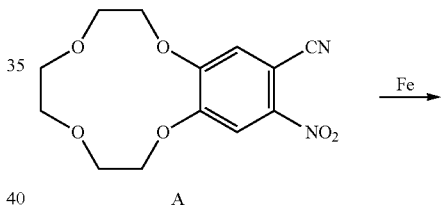

A

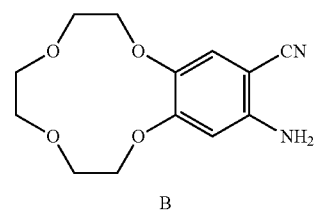

B

Compound A (25 g), ferrous powder (25 g), and 3% acetic acid in methanol solution (900 mL) were used, and other sequences and conditions were the same as described in Example 2 to give compound B (16.6 g).

Example 7

Synthesis of Compound B

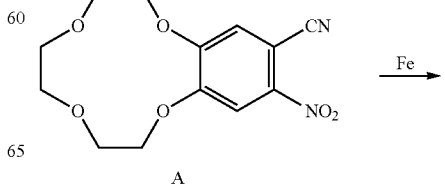

A

-continued

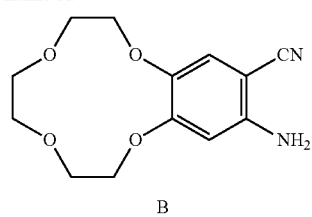

B

Compound A (40 g), ferrous powder (40 g), and 7% acetic acid in methanol solution (1200 mL) were used, and other sequences and conditions were the same as described in Example 2 to give compound B (28.4 g).

Example 8

Synthesis of Compound B

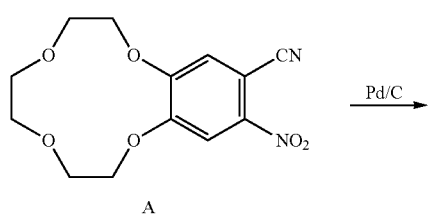

Compound A (25 g), Pd/C (5 g), and 3% acetic acid in methanol solution (900 mL) were added into 2 L of reaction flask, hydrogen gas was added, and the reaction was monitored by TLC. After its completion, the reaction mixture was filtrated, and the solvent was removed to give compound B (17 g).

Example 9

Synthesis of Compound B

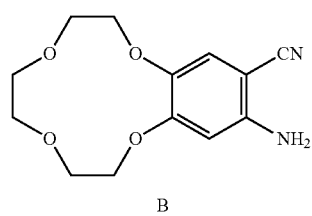

-continued

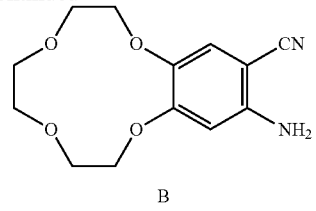

B

Compound A (40 g), magnesium ribbon (17 g), and 5% acetic acid in methanol solution (1200 mL) were used, and other sequences and conditions were the same as described in Example 2 to give compound B (25.2 g).

Example 10

Synthesis of Compound B

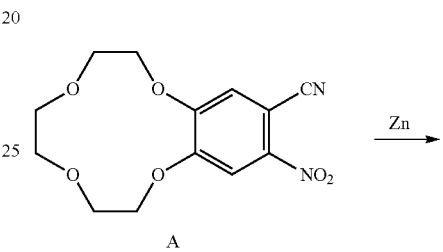

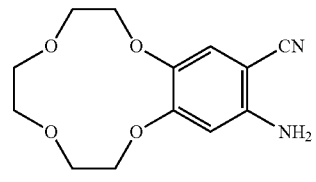 [SMILES: N#Cc1cc2c(cc1N)OCCOCCOCCO2]

B

Compound A (25 g), zinc powder (32.5 g) and 5% acetic acid in methanol solution (900 mL) were used, and other sequences and conditions were the same as described in Example 2 to give compound B (17.1 g).

Example 11

Synthesis of Compound B

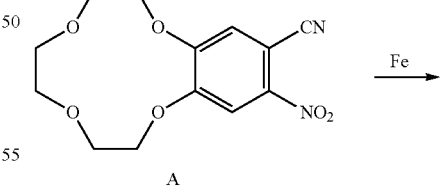

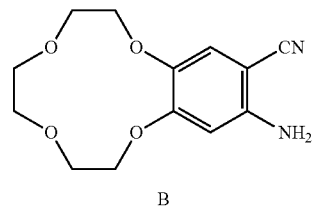

B

Compound A (25 g), ferrous powder (28 g) and 5% trifluoroacetic acid in methanol solution (700 mL) were used, and

Example 12

Synthesis of Compound C1

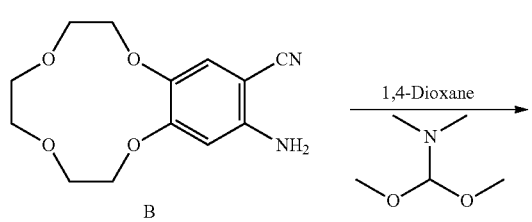

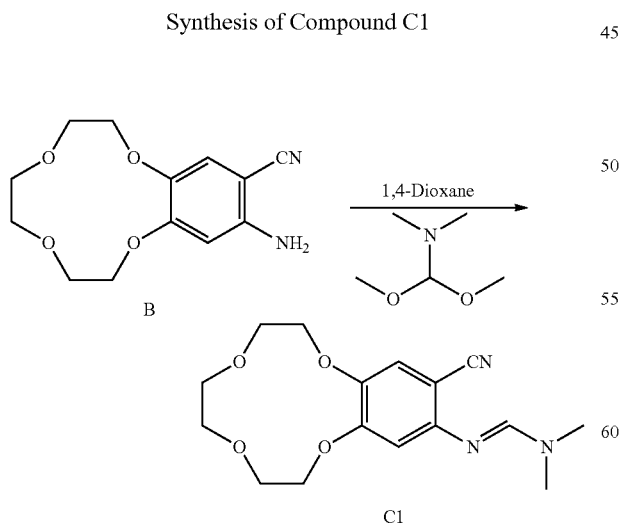

Compound B (3 g), N,N-dimethylformamide dimethyl acetal (3 g), dioxane (140 mL) were used, the time of reflux was 10-11 hours, and other sequences and conditions were the same as described in Example 3 to give compound C1 (3.2 g).

Example 13

Synthesis of Compound C1

Compound B (8 g), N,N-dimethylformamide dimethyl acetal (8 g), dioxane (180 mL) were used, the time of reflux was 12-13 hours, and other sequences and conditions were the same as described in Example 3 to give compound C1 (8.7 g).

Example 14

Synthesis of Compound C1

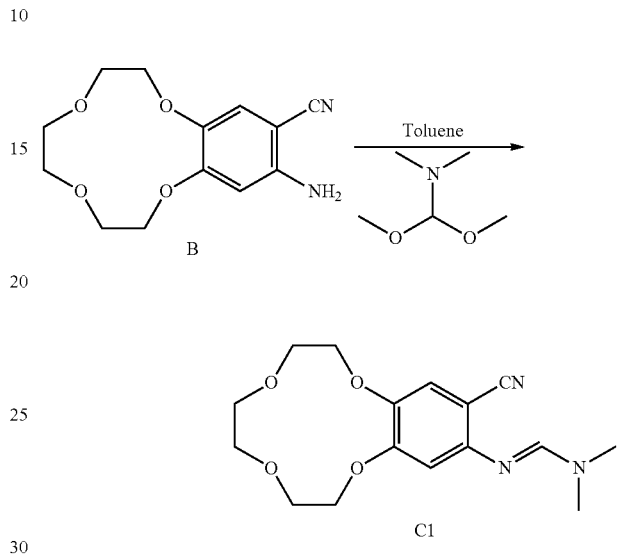

Compound B (3 g), N,N-dimethylformamide dimethyl acetal (3 g), toluene (140 mL) were used, the time of reflux was 13-15 hours, and other sequences and conditions were the same as described in Example 3 to give compound C1 (2.9 g).

Example 15

Synthesis of Compound C1

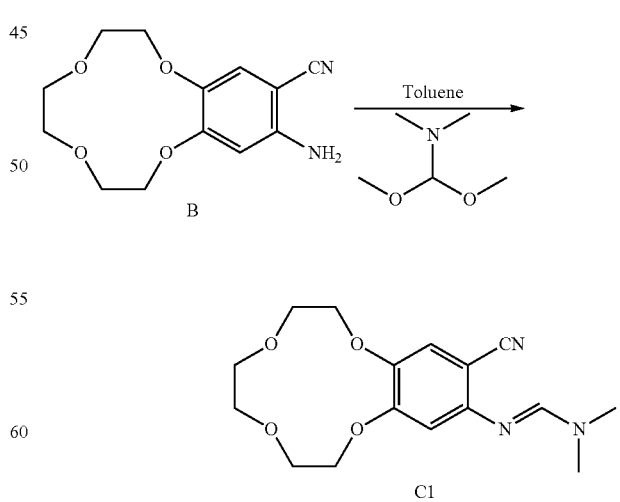

The reaction time was 10 hours, and other sequences and conditions were the same as described in Example 14 to give compound C1 (2.6 g).

Example 16

Synthesis of Compound C1

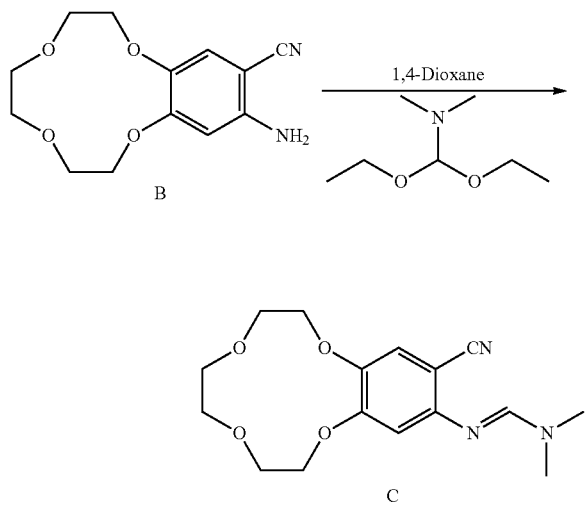

Compound B (3 g), N,N-dimethylformamide diethyl acetal (3.7 g) and dioxane (140 mL) were added into 500 mL of three-necked flask, heated to reflux, and the reaction was monitored by TLC. The reaction time is about 11-12 hours. After its completion, the reaction mixture was cooled to room temperature and evaporated to give compound C1 (2.5 g).

Example 17

Synthesis of Compound C1

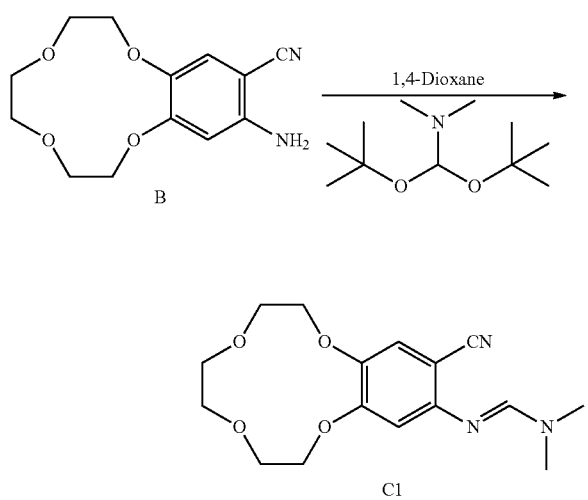

Compound B (3 g) and N,N-Dimethylformamide di-t-butyl-acetal (5.1 g) were dissolved in dioxane (140 mL), heated to reflux, and the reaction was monitored by TLC. The reaction time is about 11-12 hours. After its completion, the reaction mixture was cooled to room temperature and evaporated to give compound C1 (2.6 g).

Example 18

Synthesis of Compound C1

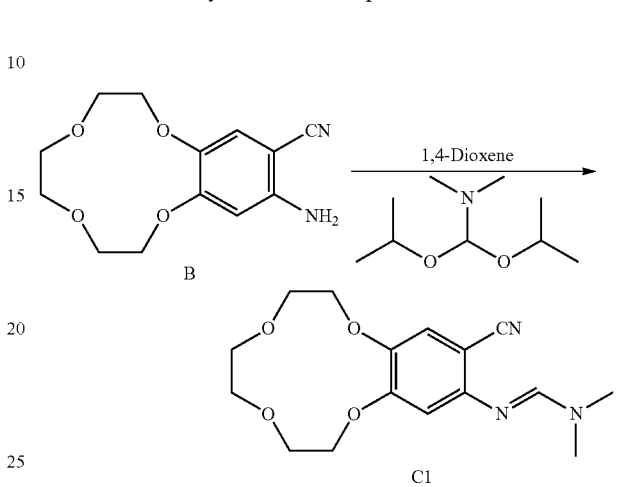

Compound B (3 g) and N,N-dimethylformamide diisopropyl acetal (4.4 g) were dissolved in dioxane (140 mL), heated to reflux, and the reaction was monitored by TLC. The reaction time is about 11-12 hours. After its completion, the reaction mixture was cooled to room temperature and evaporated to give compound C1 (2.4 g).

Example 19

Synthesis of Icotinib

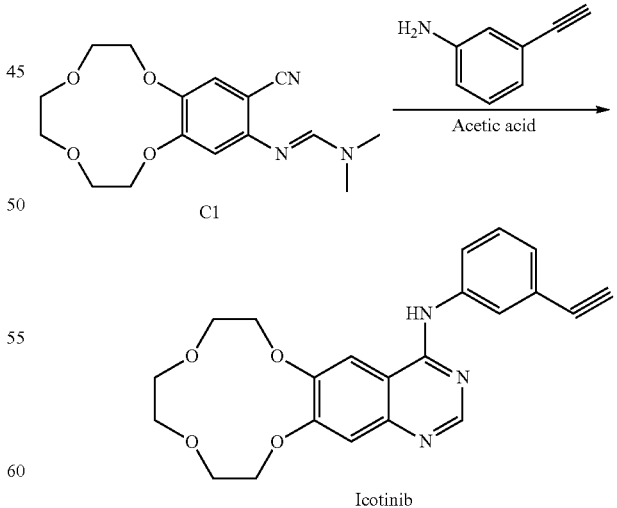

Compound C1 (3 g), m-aminophenyl acetylene (1.3 g), and acetic acid (130 mL) were added into 250 mL of reaction flask, heated to 70-80° C., and the reaction was monitored by TLC. After its completion, the reaction mixture was evaporated, methanol was added, and then the mixture was shock dispersed, filtrated, and washed with methanol to give Icotinib (2.8 g).

Example 20

Synthesis of Icotinib

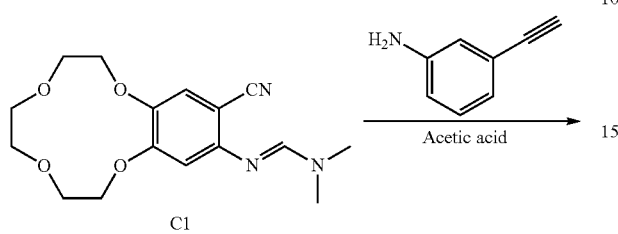

Compound C1 (8 g) and m-aminophenyl acetylene (3.5 g) were dissolved in acetic acid (380 mL), heated to 100-120° C., and the reaction was monitored by TLC. After its completion, the reaction mixture was evaporated, ethanol was added, and then the mixture was shock dispersed, filtrated, and washed with ethanol to give Icotinib (7.2 g).

Example 21

Synthesis of Icotinib

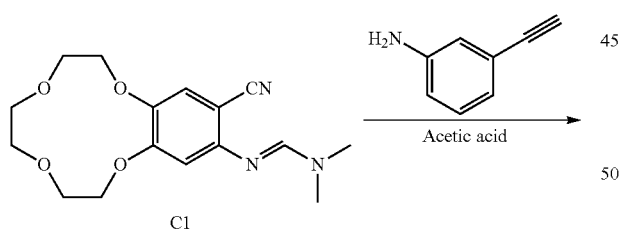

The reaction temperature of 120-150° C., and other sequences and conditions were the same as described in Example 4 to give Icotinib (2.2 g).

Example 22

Synthesis of Icotinib

Compound C1 (3 g), m-aminophenyl acetylene (1.8 g), and acetic acid (130 mL) were added into 250 mL of reaction flask, heated to 90-100° C., and the reaction was monitored by TLC. After its completion, the reaction mixture was evaporated, isopropanol was added, and the mixture was then shock dispersed, filtrated, and washed with isopropanol to give Icotinib (2.9 g).

Example 23

Synthesis of Icotinib

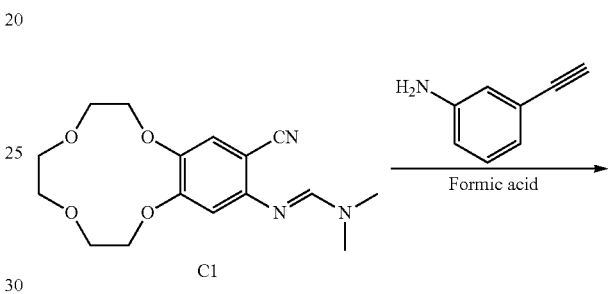

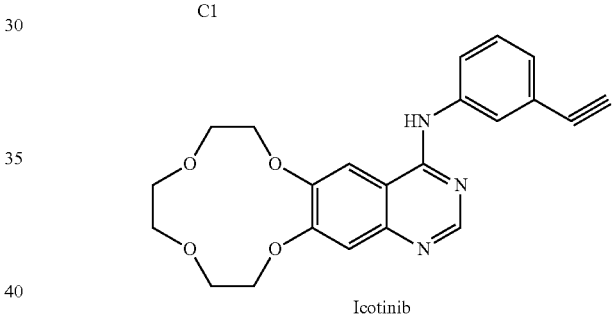

Compound C1 (3 g) and m-aminophenyl acetylene (1.3 g) were dissolved in formic acid (130 mL), heated to 80-90° C., and the reaction was detected by TLC. After its completion, the reaction mixture was evaporated, methanol was added, and then the mixture was shocked dispersed, filtrated, and washed with methanol to give Icotinib (2.7 g).

Example 24

Synthesis of Icotinib

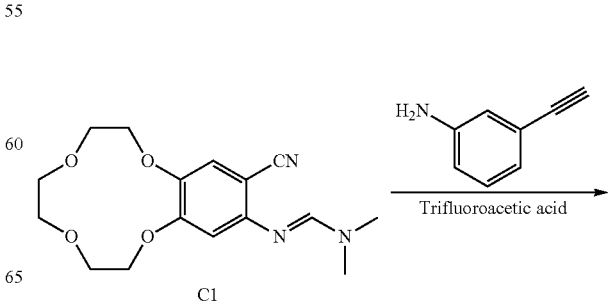

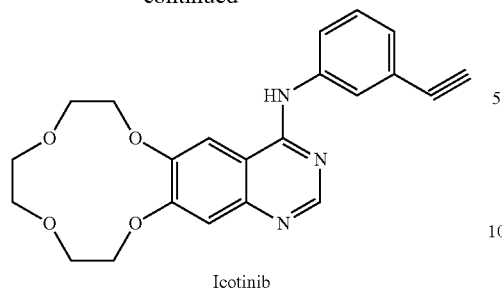

Icotinib

Compound C1 (3 g) and m-aminophenyl acetylene (1.3 g) were dissolved in trifluoroacetic acid (130 mL), heated to 70-80° C., and the reaction was monitored by TLC. After its completion, the reaction mixture was evaporated, methanol was added, and then the mixture was shock dispersed, filtrated, and washed with methanol to give Icotinib (2.7 g).

Example 25

Synthesis of Icotinib Hydrochloride

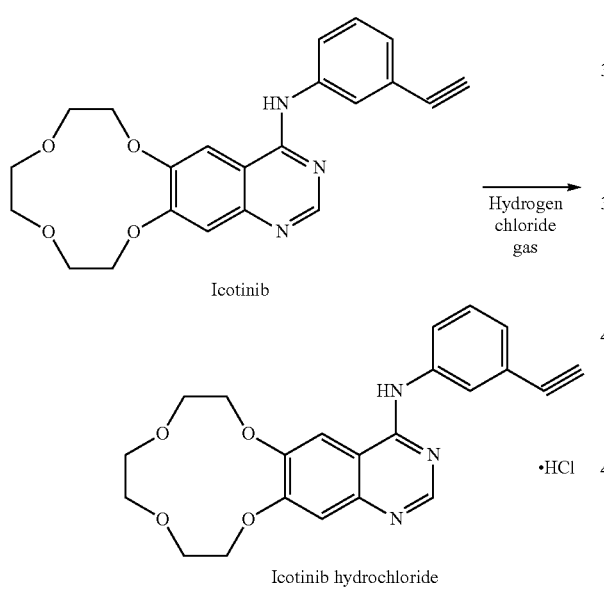

Icotinib (500 mg) was added into 100 mL of reaction flask and dissolved with 30 mL of ethanol. Hydrogen chloride gas was added while stirring. After its completion, the reaction mixture was filtered to give crude product. The crude product was further purified by recrystallization with isopropyl alcohol to give Icotinib hydrochloride (515 mg).

Example 26

Synthesis of Icotinib Hydrochloride

Icotinib (500 mg) was added into 100 mL of reaction flask and dissolved with 40 mL of THF. Hydrogen chloride gas was added while stirring. After its completion, the reaction mixture was filtered to give crude product. The crude product was further purified by recrystallization with isopropyl alcohol to give Icotinib hydrochloride (500 mg).

Example 27

Synthesis of Icotinib Hydrochloride

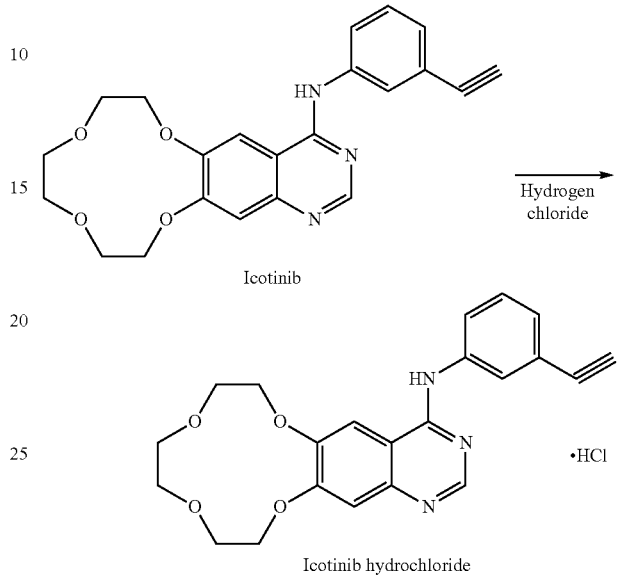

Icotinib (5 00 mg) was added into 100 mL of reaction flask and dissolved with 50 mL of isopropyl alcohol. Hydrogen chloride gas was added while stirring. After its completion, the reaction mixture was filtered to give crude product. The crude product was further purified by recrystallization with isopropyl alcohol to give Icotinib hydrochloride (500 mg).

Example 28

Synthesis of Icotinib Hydrochloride

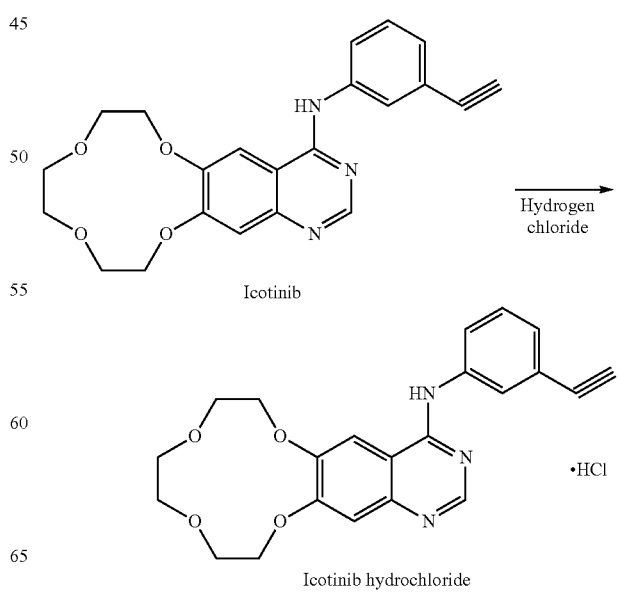

Icotinib (1000 mg) was added into 100 mL reaction flask and dissolved with 60 mL of methanol. The concentrated hydrochloric acid was added dropwise while stirring till PH was adjusted to 2.0. After its completion, the reaction mixture was filtered to give crude product. The crude product was further purified by recrystallization with isopropyl alcohol to give Icotinib hydrochloride (1000 mg).

The following exemplary compounds in Table 1 were prepared by similar methods as described above.

TABLE 1

| Example | Reactant 1 | Reactant 2 | Product | [M + H]$^+$ |
|---|---|---|---|---|
| 29 | | | | 348.3 |
| 30 | | | | 334.3 |
| 31 | | | | 348.3 |
| 32 | | | | 376.3 |
| 33 | | | | 320.3 |
| 34 | | | | 348.3 |
| 35 | | | | 318.4 |

TABLE 1-continued

| Example | Reactant 1 | Reactant 2 | Product | [M + H]+ |
|---|---|---|---|---|
| 36 | | | | 346.3 |
| 37 | | | | 320.3 |

What is claimed is:

1. A compound of formula A, B, or C:

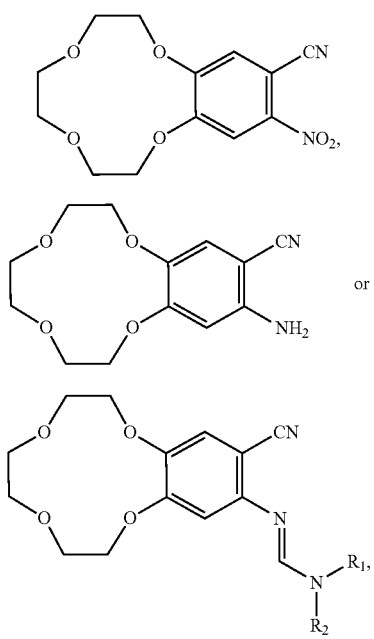

wherein:

each of $R_1$ and $R_2$ independently is methyl, ethyl, propyl, or isopropyl; or $R_1$ and $R_2$, together with the N atom to which they are attached, form a 3 to 7-membered ring.

2. The compound of claim 1, wherein each of $R_1$ and $R_2$ independently is methyl or ethyl.

3. The compound of claim 1, wherein $R_1$ and $R_2$ are both methyl.

4. The compound of claim 1, wherein $R_1$ and $R_2$ are both ethyl.

5. The compound of claim 1, wherein $R_1$ and $R_2$, together with the N atom to which they are attached, form a 3, 4, or 5-membered ring.

6. The compound of claim 1, wherein $R_1$ and $R_2$, together with the N atom to which they are attached, form a 5, 6, or 7-membered ring.

7. A method for preparing compound C comprising the step of converting compound B into compound C:

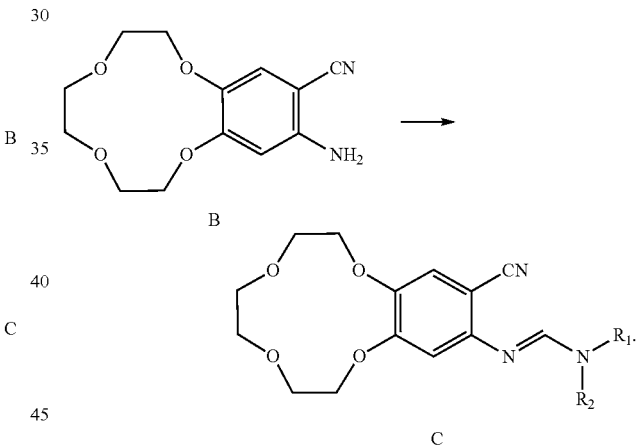

8. The method of claim 7, wherein the conversion of compound B to compound C is by reacting compound B with a compound of the formula

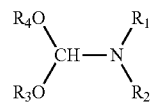

comprising the step of:

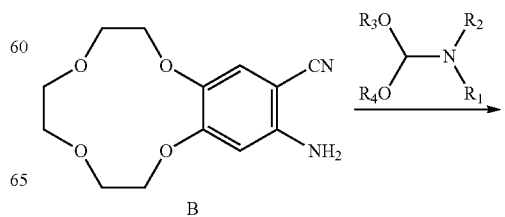

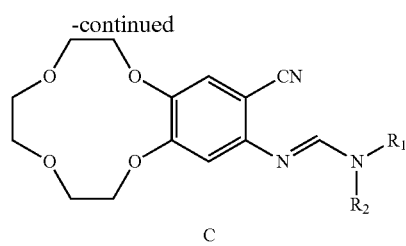

C wherein:

each of $R_3$ and $R_4$ independently is methyl, ethyl, propyl, isopropyl, normal-butyl, sec-butyl, tert-butyl, isobutyl, or benzyl; or $R_3$ and $R_4$ together form a 3 to 7-membered ring.

9. The method of claim 8, wherein each of $R_3$ and $R_4$ independently is methyl, ethyl, isopropyl, tert-butyl, or benzyl.

10. The method of claim 8, wherein $R_3$ and $R_4$ are both methyl.

11. The method of claim 8, wherein $R_3$ and $R_4$ are both ethyl.

12. The method of claim 8, wherein compound B and

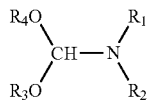

react in dioxane or toluene under reflux.

13. The method of claim 12, wherein the molar ratio of compound B and

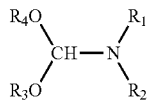

is 1:1.5-1:2.8.

14. The method of claim 12, wherein the molar ratio of compound B and

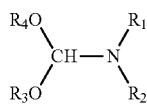

is 1:2.0-1:2.5.

15. The method of claim 12, wherein 11-30 mmol compound B and 25-67 mmol

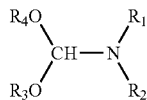

react in 140-180 mL of dioxane under reflux for 10-15 hours.

16. The method of claim 12, wherein

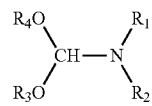

is N,N-dimethylformamide dimethyl acetal, N,N-dimethylformamide diethyl acetal, or N,N-dimethylformamide di-tert-butyl acetal.

17. A method for preparing compound B comprising the step of converting compound A to compound B:

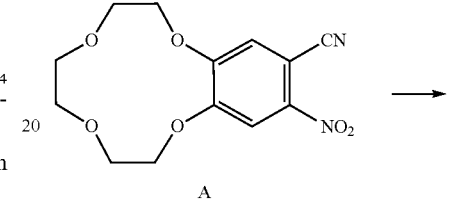

A

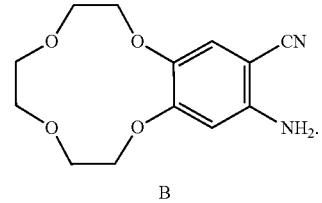

B

18. The method of claim 17, wherein compound A is converted to compound B by reacting compound A with a proton-donating agent, metal hydride, hydrazine, or alkali ammonia solution via catalytic hydrogenation reaction or metal-involved reduction reaction; the metal is Mg, Al, Zn, Fe, Sn, Pb or Cu; the proton-donating agent is acetic acid, formic acid and/or trifluoroacetic acid (TFA); the catalyst applied in the catalytic hydrogenation reaction is Pd/Carbon or Raney Ni; the metal hydride is sodium hydride or potassium hydride; and the alkali metal is sodium or potassium.

19. The method of claim 18, wherein compound A, ferrous powder, and acetic acid in methanol solution are fully mixed, and heated to reflux until the reaction is complete.

20. The method of claim 18, wherein 85 mmol-0.2 mol compound A, 0.45-0.71 mol of ferrous powder, and 900-1200 mL of acetic acid in methanol solution are fully mixed, and heated to reflux until the reaction is complete, and the mass percentage of acetic acid in the acetic acid in methanol solution is 3-7%.

21. A method for preparing Icotinib comprising a step of reacting compound C with m-aminophenyl acetylene in the presence of an organic acid:

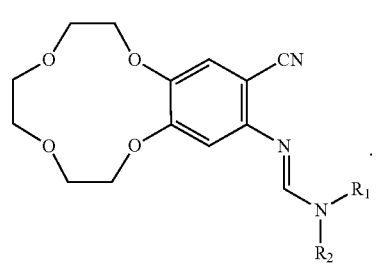

C

22. The method of claim 21, wherein the molar ratio of compound C and m-aminophenyl acetylene is 1:1-1:2.

23. The method of claim 21, wherein the molar ratio of compound C and m-aminophenyl acetylene is 1:1-1:1.5.

24. The method of claim 21, wherein the organic acid is acetic acid, formic acid, and/or trifluoroacetic acid.

25. The method of claim 21, wherein compound C, m-aminophenyl acetylene, and the organic acid are fully mixed and react at 70-150° C.

26. The method of claim 21, wherein the reaction temperature is 90-120° C., and the organic acid is acetic acid.

27. The method of claim 21, wherein compound C is N,N-dimethyl-N'-(6-cyano-3,4-benzo-12-crown-4)formamidine; compound C, m-aminophenyl acetylene, and acetic acid are fully mixed and react at 70-150° C.

28. The method of claim 21, wherein compound C is N,N-dimethyl-N'-(6-cyano-3,4-benzo-12-crown-4)formamidine; 9-25 mmol of compound C, 15-21 mmol of m-aminophenyl acetylene, and 150-320 mL of acetic acid are fully mixed and react at 90-120° C., or 12-20 mmol of compound C, 17-20 mmol of m-aminophenyl acetylene, and 200-260 mL of acetic acid are fully mixed and react at 95-105° C.

29. A method for preparing Icotinib hydrochloride comprising the steps of:
preparing Icotinib by reacting compound C with m-aminophenyl acetylene in the presence of an organic acid;
dissolving Icotinib in a lower alcohol to give a reaction mixture;
adding hydrogen chloride gas or hydrochloric acid while stirring the reaction mixture; and then
filtering the reaction mixture after the reaction is complete.

30. The method of claim 29, wherein the lower alcohol comprises methanol, ethanol, and/or isopropanol.

31. The method of claim 29, wherein the amount of Icotinib is 1.3-2.6 mmol; the lower alcohol is methanol, and its volume is 30-60 mL.

32. The method of claim 29 wherein the amount of Icotinib is 1.8 mmol; the lower alcohol is methanol, and its volume is 40 mL.

* * * * *